(12) United States Patent
Iwamura et al.

(10) Patent No.: US 9,933,358 B2
(45) Date of Patent: Apr. 3, 2018

(54) AUTOMATIC ANALYZER

(75) Inventors: Kanako Iwamura, Haga-gun (JP); Shoichi Kanayama, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/401,047

(22) Filed: Feb. 21, 2012

(65) Prior Publication Data
US 2012/0148450 A1 Jun. 14, 2012

Related U.S. Application Data

(63) Continuation of application No. PCT/JP2011/077902, filed on Dec. 2, 2011.

(30) Foreign Application Priority Data

Dec. 3, 2010 (JP) .................. 2010-270239

(51) Int. Cl.
*G01N 21/59* (2006.01)
*G01N 21/25* (2006.01)
(Continued)

(52) U.S. Cl.
CPC ......... *G01N 21/253* (2013.01); *G01N 35/025* (2013.01); *G01N 35/04* (2013.01);
(Continued)

(58) Field of Classification Search
None
See application file for complete search history.

(56) References Cited

U.S. PATENT DOCUMENTS 4,320,971 A * 3/1982 Hashimoto et al. .......... 356/328
4,896,963 A * 1/1990 Kato ............................ 356/328
(Continued)

FOREIGN PATENT DOCUMENTS

CN 101441165 A 5/2009
JP 58-92841 A 6/1983
(Continued)

OTHER PUBLICATIONS

International Search Report dated Dec. 27, 2011 in PCT/JP2011/077902.
(Continued)

*Primary Examiner* — P. Kathryn Wright
(74) *Attorney, Agent, or Firm* — Oblon, McClelland, Maier & Neustadt, L.L.P.

(57) ABSTRACT

According to one embodiment, an automatic analyzer comprises a light source, a spectroscope, a photo detection unit, a storage unit, a selection unit, and a calculation unit. The storage unit stores photo detector identifiers related to photo detectors and wavelength band identifiers in association with each other. The selection unit selects a specific photo detector from photo detectors. The specific photo detector corresponds to a specific photo detector identifier associated with a wavelength band identifier of a wavelength band according to a measurement item of a sample. The calculation unit calculates an absorbance related to the measurement item based on a signal from the selected specific photo detector.

8 Claims, 8 Drawing Sheets

(51) Int. Cl.
*G01N 35/02* (2006.01)
*G01N 35/04* (2006.01)

(52) U.S. Cl.
CPC ........ *G01N 2035/0455* (2013.01); *G01N 2201/0415* (2013.01); *G01N 2201/124* (2013.01); *G01N 2201/127* (2013.01); *G01N 2201/1245* (2013.01)

(56) References Cited

U.S. PATENT DOCUMENTS

| | | | | |
|---|---|---|---|---|
| 5,422,483 | A * | 6/1995 | Ando et al. | 250/339.02 |
| 6,124,134 | A * | 9/2000 | Stark | A61B 5/14532 |
| | | | | 250/339.02 |
| 7,830,518 | B2 | 11/2010 | Kanayama | |
| 2006/0066850 | A1* | 3/2006 | Kimura | 356/328 |
| 2008/0297796 | A1* | 12/2008 | Lukas et al. | 356/326 |
| 2010/0007886 | A1* | 1/2010 | Okabayashi | 356/409 |

FOREIGN PATENT DOCUMENTS

| | | |
|---|---|---|
| JP | 1-145552 | 6/1989 |
| JP | 4-63600 | 2/1992 |
| JP | 6-50889 | 2/1994 |
| JP | 8-114541 | 5/1996 |
| JP | 2004-191244 | 7/2004 |
| JP | 2005-43153 | 2/2005 |
| JP | 2008-98228 | 4/2006 |
| JP | 2008-298776 | 12/2008 |
| JP | 2010-60525 | 3/2010 |

OTHER PUBLICATIONS

Chinese Office Action dated Sep. 5, 2013, in China Patent Application No. 201180003355.0 (with English Translation).
International Written Opinion dated Dec. 27, 2011, in PCT/JP2011/077902 filed Dec. 2, 2011 (English translation).
Office Action dated Jul. 19, 2016, in Japanese Patent Application No. 2011-264869.
International Search Report dated Dec. 27, 2011 in PCT/JP2011/077902 filed Dec. 2, 2011.
International Written Opinion dated Dec. 27, 2011 in PCT/JP2011/077902 filed Dec. 2, 2011.

* cited by examiner

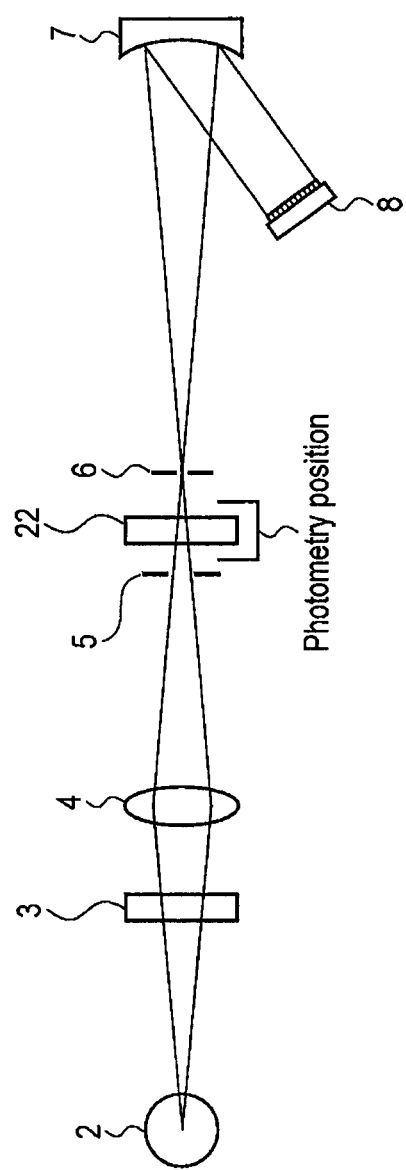
F I G. 2

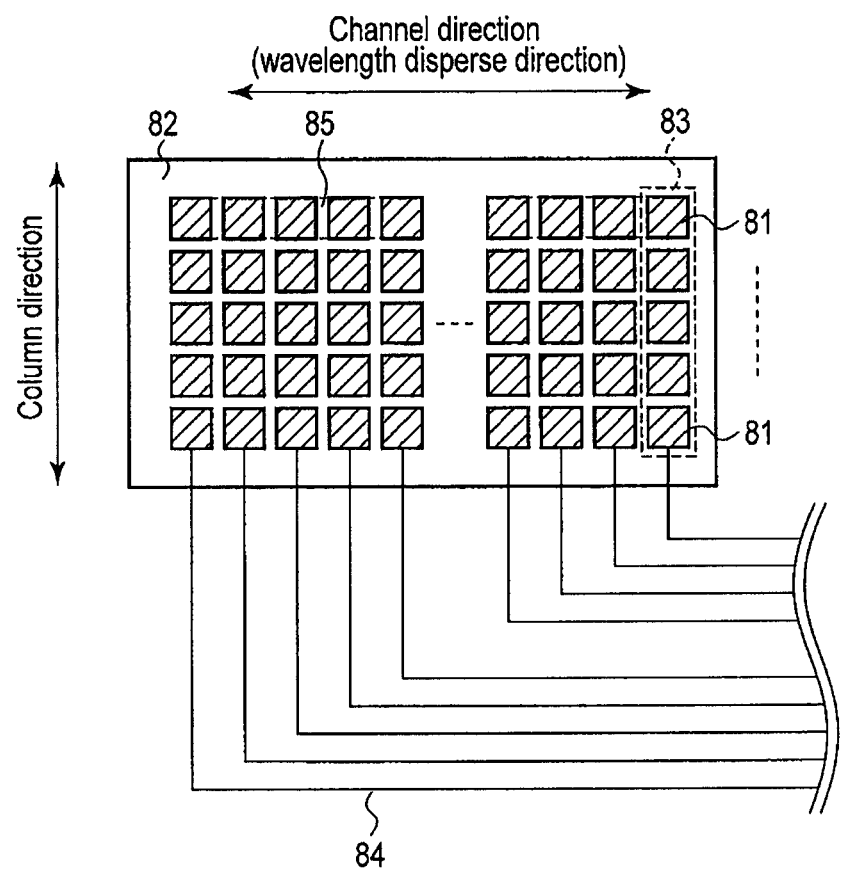
F I G. 3

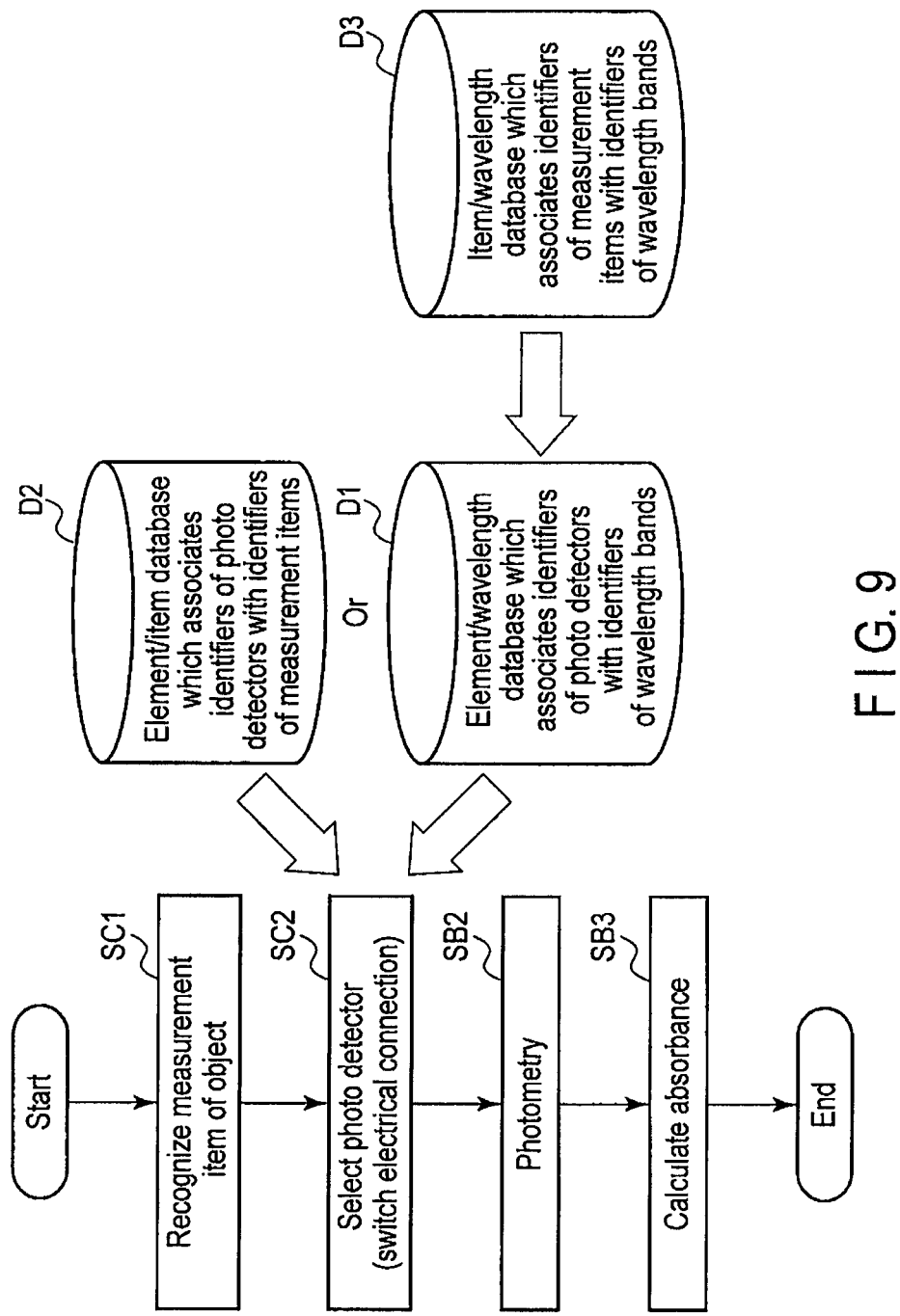
F I G. 9

AUTOMATIC ANALYZER

CROSS REFERENCE TO RELATED APPLICATIONS

This application is a Continuation Application of PCT Application No. PCT/JP2011/077902, filed Dec. 2, 2011 and based upon and claiming the benefit of priority from prior Japanese Patent Application No. 2010-270239, filed Dec. 3, 2010, the entire contents of all of which are incorporated herein by reference.

FIELD

Embodiments described herein relate generally to an automatic analyzer.

BACKGROUND

An automatic analyzer spectrally separates light, which has been transmitted through a liquid mixture of a sample and reagent, using a spectroscope, and receives light components from the spectroscope by a photo detection unit. The light components from the spectroscope have different wavelengths depending on physical positions. The photo detection unit has a plurality of photo detectors. Respective photo detectors receive light components related to wavelengths according to their locations.

The photo detectors are often deviated from their original positions at the time of assembling or the like of the apparatus. Such deviations are called wavelength accuracy deviations. When the wavelength accuracy deviations have occurred, position adjustments of the photo detectors are executed. However, the position adjustments of the photo detectors impose a heavy load on the assembler.

It is an object to provide an automatic analyzer which can reduce a load on position adjustments of photo detectors.

BRIEF DESCRIPTION OF THE DRAWINGS

FIG. 2 is a view illustrating the structure of an optical system included in a photometry unit shown in FIG. 1.

FIG. 3 is a view showing an example of a layout pattern of photo detectors included in a photo detection unit shown in FIG. 2.

FIG. 9 is a flowchart showing the typical sequence of processing in a photometry stage of the automatic analyzer according to the first modification of this embodiment.

DETAILED DESCRIPTION

In general, according to one embodiment, an automatic analyzer comprising a light source, a spectroscope, a photo detection unit, a storage unit, a selection unit, a calculation unit. The light source emits light. The spectroscope disperses light, which is emitted by the light source and is transmitted through a liquid mixture of a sample and a reagent, into different wavelengths. The photo detection unit includes a plurality of photo detectors which receive light from the spectroscope, each of the photo detectors receive light related to a wavelength band corresponding to a location of that photo detector, and generates a signal according to the received light. The storage unit stores a plurality of photo detector identifiers related to the plurality of photo detectors and a plurality of wavelength band identifiers in association with each other. The selection unit selects a specific photo detector from the photo detectors, the specific photo detector corresponding to a specific photo detector identifier associated with a wavelength band identifier of a wavelength band according to a measurement item of the sample. The calculation unit calculates an absorbance related to the measurement item based on a signal from the selected specific photo detector.

An automatic analyzer according to this embodiment will be described hereinafter with reference to the drawings.

Figure 1:
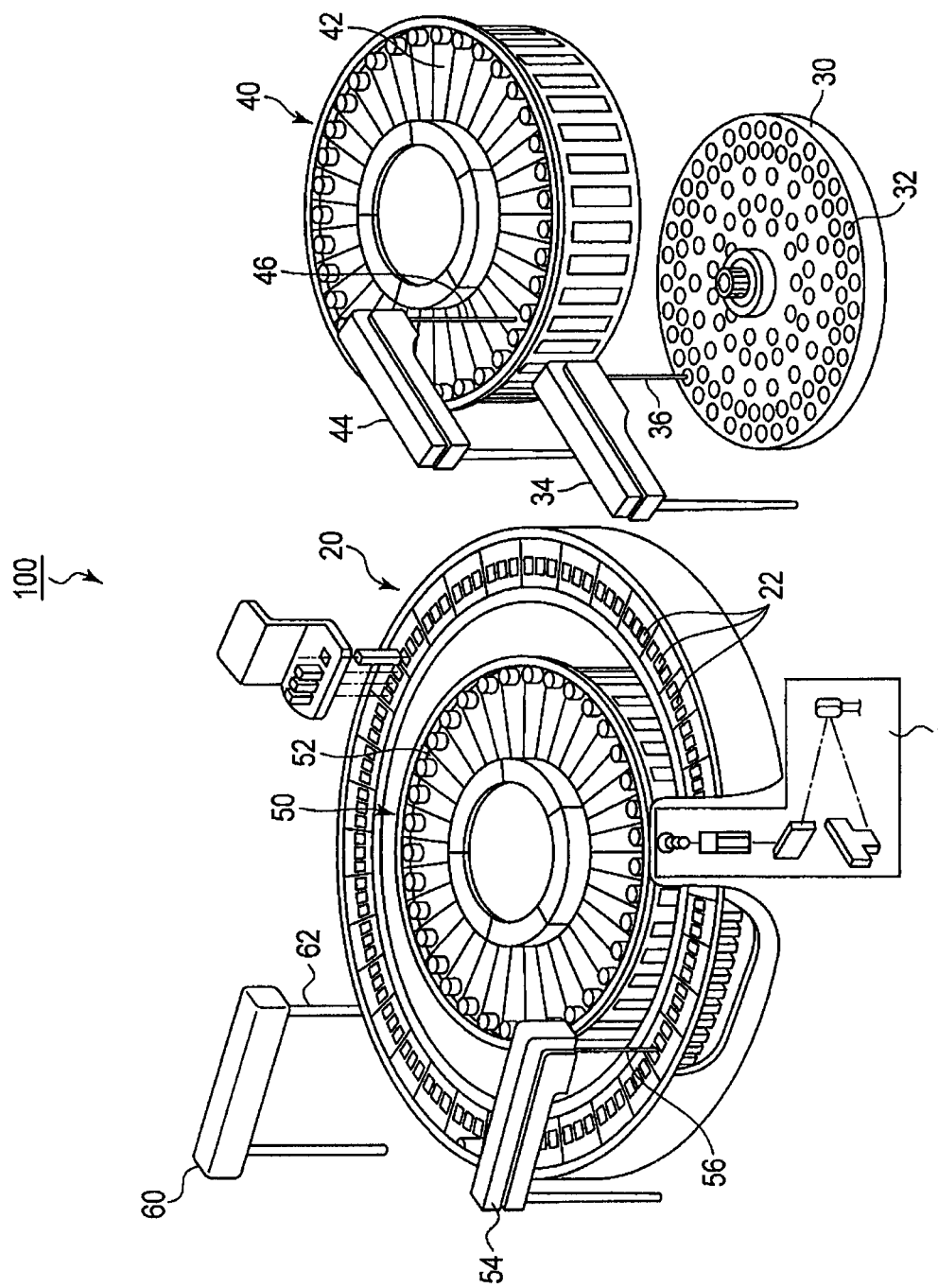
FIG. 1 is a schematic view showing the arrangement of an automatic analyzer according to this embodiment.

FIG. 1 is a schematic view showing the arrangement of an automatic analyzer 100 according to this embodiment. As shown in FIG. 1, a reaction disc 20 is arranged at nearly a central portion of a stage of the automatic analyzer 100. The reaction disc 20 holds a plurality of reaction containers (cuvettes) 22 which are laid out on the circumference. The reaction disc 20 repetitively pivots and stops at a predetermined cycle.

A disc-shaped sample disc 30 is disposed in the vicinity of the reaction disc 20. The sample disc 30 holds a plurality of sample containers 32, which are laid out concentrically. Each sample container 32 contains a sample. The sample disc 30 is rotated about a rotation axis, and locates a sample container 32 which contains a sample to be dispensed at a sample suction position on the sample disc 30.

A first reagent storage 40 is disposed in the vicinity of the reaction disc 20. The first reagent storage 40 has a disc-shaped first reagent disc. The first reagent disc holds a plurality of first reagent containers 42 which are laid out concentrically. Each first reagent container 42 contains a first reagent that causes chemical reactions with components which are included in a sample and correspond to respective measurement items. The first reagent disc is rotated about a rotation axis, and locates a first reagent container 42 which contains a first reagent to be dispensed at a first reagent suction position on the first reagent storage 40.

A second reagent storage 50 is disposed inside the reaction disc 20. The second reagent storage 50 has a disc-shaped second reagent disc. The second reagent disc holds a plurality of second reagent containers 52 which are laid out on the circumference. Each second reagent container 52 contains a second reagent corresponding to the first reagent. The second reagent disc is rotated about a rotation axis, and locates a second reagent container 52 which contains a second reagent to be dispensed at a second reagent suction position on the second reagent storage 50.

A sample arm 34 is disposed between the reaction disc 20 and sample disc 30. A sample probe 36 is attached to the distal end of the sample arm 34. The sample probe 36 sucks in or discharges a sample by an electrically operated pump (not shown). The sample arm 34 moves the sample probe 36 to pivot between the sample suction position on the sample disc 30 and the sample discharge position on the reaction disc 20. The sample arm 34 moves the sample probe 36 upward and downward.

A first reagent arm 44 is disposed between the reaction disc 20 and first reagent storage 40. A first reagent probe 46 is attached to the distal end of the first reagent arm 44. The first reagent probe 46 sucks in or discharges a first reagent by a pump (not shown). The first reagent arm 44 moves the first reagent probe 46 to pivot between the first reagent suction position on the first reagent storage 40 and the first reagent discharge position on the reaction disc 20. Also, the first reagent arm 44 moves the first reagent probe 46 upward and downward.

A second reagent arm 54 is disposed in the vicinity of the outer circumference of the reaction disc 20. A second reagent probe 56 is attached to the distal end of the second reagent arm 54. The second reagent probe 56 sucks in or discharges a second reagent by a pump (not shown). The second reagent arm 54 moves the second reagent probe 56 to pivot between the second reagent suction position on the second reagent storage 50 and the second reagent discharge position on the reaction disc 20. Also, the second reagent arm 54 moves the second reagent probe 56 upward and downward.

A stirring unit arm 60 is disposed in the vicinity of the outer circumference of the reaction disc 20. The stirring unit 60 stirs a liquid mixture of a sample and first reagent or that of a sample, first reagent, and second reagent in the cuvette 22 at a stirring position on the reaction disc 20 by a stirrer 62.

A photometry unit 1 is arranged inside the stage. The photometry unit 1 executes photometry so as to calculate absorbance related to measurement items of an object to be measured.

FIG. 2 illustrates the structure of an optical system included in the photometry unit 1. As shown in FIG. 2, the photometry unit 1 mounts a light source 2 which emits light. As the light source 2, a lamp such as a halogen lamp or tungsten lamp is used. Note that an LED (light emitting diode) may be used as the light source 2. When the reaction disc pivots, the cuvette 22 passes a predetermined position (photometry position) PP in the optical system. Along an optical path between the lamp 2 and the photometry position PP, an infrared cut filter 3, lens 4, and slit 5 are arranged in turn from the lamp 2 side. The infrared cut filter 3 mainly moderately absorbs infrared rays unnecessary in measurements from the lamp 2. The lens 4 condenses light transmitted through the infrared cut filter 3. The slit 5 limits a width of the light condensed by the lens 4. The light, which has passed through the slit 5, is transmitted through a liquid mixture in the cuvette 22.

The light transmitted through the liquid mixture is received by a photo detection unit 8 via some optical devices 6 and 7. Along an optical path between the photometry position PP and photo detection unit 8, a slit 6 and spectroscope 7 are arranged in turn from the photometry position PP side. The slit 6 limits a width of the light transmitted through the liquid mixture in the cuvette 22. The spectroscope 7 spectrally separates the light, which has passed through the slit 6. As the spectroscope 7, for example, a diffraction grating is adopted. The diffraction grating is configured by, for example, a concave mirror on a mirror surface of which a plurality of grooves (grid lines) are formed at equal intervals. Light with which the diffraction grating is irradiated is diffused for respective wavelengths by the grid lines on the diffraction grating. In other words, the diffraction grating separates light into a plurality of rays (monochromatic light rays) related to a plurality of wavelengths. The plurality of rays (primary diffracted light rays) from the diffraction grating are received by the photo detection unit 8.

The photo detection unit 8 is disposed on optical paths of the plurality of rays (primary diffracted light rays) coming from the spectroscope 7 so as to cover all wavelength widths which can be used in absorbance calculations. The photo detection unit 8 includes a plurality of photo detectors.

FIG. 3 shows an example of a layout pattern of photo detectors 81. As shown in FIG. 3, the plurality of photo detectors 81 are two-dimensionally laid out on a substrate 82 or the like of the photo detection unit 8. As the photo detectors 81, a CCD image sensor or photo diode array (PDA: photo detector array) on which photoelectric conversion elements such as CCDs (charge coupled devices) or photo detectors are two-dimensionally laid out is used. Each photo detector 81 to be adopted is sensitive to near-ultraviolet rays, visible rays, or near-infrared rays. Typically, all the photo detectors 81 to be used included in the photo detection unit 8 have the same performance.

One layout direction of the photo detectors 81 is parallel to a diffusion direction of wavelengths (a spectrum layout direction). The diffusion direction of wavelengths is specified to agree with a channel direction of the photo detectors 81. For example, 125 photo detectors 81 (for 125 channels) are laid out along the channel direction. The other layout direction of the photo detectors 81 is parallel to, for example, an orthogonal direction of the channel direction and an optical axis direction of primary diffracted light from the spectroscope 7. Ideally, the wavelengths of the plurality of rays from the spectroscope 7 do not change along this orthogonal direction. The photo detectors 81 belonging to a single channel receive light components having a nearly single wavelength. A plurality of photo detectors 81 which belong to an identical channel will be referred to as a photo detector column 83 hereinafter. Also, this orthogonal direction will be referred to as a column direction hereinafter. Note that the number of photo detectors 81, which are laid out along the channel direction, is not limited to 125. For example, 250 elements which are equal to or larger than 125 elements or 80 elements which are equal to or smaller than 125 elements may be arranged.

A length of a photo detection surface related to the channel direction of one photo detector 81 is designed to be, for example, 1 to 4 nm. Since the photo detection surface of each photo detector 81 has a width having a physically nonnegligible length, the photo detector 81 cannot receive light of only a single wavelength, and receives rays within a wavelength width according to the length of the photo detection surface related to the channel direction. A wavelength range within the wavelength width having a center wavelength of light received by one photo detector 81 as the center will be referred to as a wavelength band hereinafter. The wavelength band is decided according to a spatial location of the photo detector 81 and the length of the photo detection surface in the channel direction. For example, when the center wavelength of 340 nm and the wavelength width is ±2 nm, the wavelength band ranges from 338 nm to 342 nm. Note that all the photo detectors 81 in the photo detection unit 8 have the same photo detection surface area. Therefore, the wavelength band associated with each photo detector 81 is decided according to its spatial location. To the photo detectors 81, signal lines 84 via which amplifiers in a subsequent stage are electrically connected are connected.

When 125 photo detectors 81 are laid out along the channel direction, and a wavelength band used in absorbance calculations ranges from 330 nm to 830 nm, a wavelength width per photo detector 81 corresponds to 4 nm. Therefore, when the photo detectors 81 can be laid out without any gap, the width of the photo detection area of each photo detector 81 is preferably 4 nm. However, as shown in FIG. 3, the photo detectors 81 are laid out to have gaps 85 between them. The gaps 85 are set to have equal intervals. When the gaps 85 are too large, a probability of a reception failure of light of a desired wavelength unwantedly increases. In this case, in order to reduce this probability, it is desirable to lay out the photo detector 81 so that a photo detection area S1 of each photo detector 81 and an area S0 of each gap 85 along the channel direction satisfy (S1/S1+S0))<0.2. In other words, the gap 85 is preferably designed so that its wavelength width is smaller than 20% of that of one photo detector 81.

Note that in this embodiment, the gaps 85 need not always be laid out so as to satisfy (S1/S1+S0))<0.2, and they may be laid out to satisfy (S1/S1+S0))<0.5. Note that the photo detectors 81 may be laid out without any gap.

In subsequent absorbance calculations, not only light of only a measurement wavelength but also rays for a wavelength width having the measurement wavelength as the center are used. For example, rays for a wavelength width of about ±10 nm having the measurement wavelength as the center are used. Therefore, for one measurement wavelength, outputs from the four or five photo detectors 81 along the channel direction are used in absorbance calculations.

Figure 4:
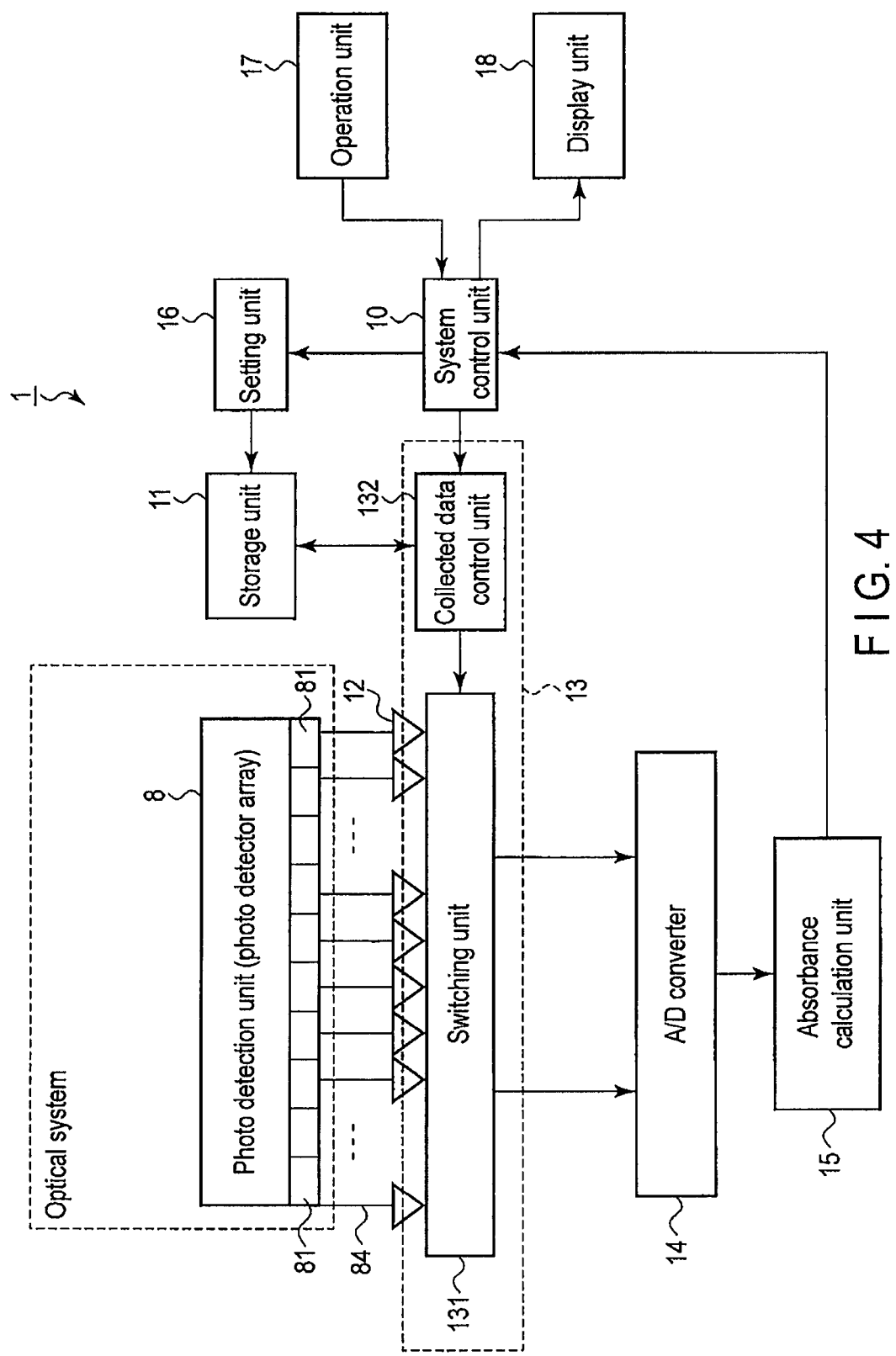
FIG. 4 is a block diagram showing the overall arrangement of the photometry unit shown in FIG. 1.

The overall arrangement of the photometry unit 1 according to this embodiment will be described below with reference to FIG. 4. As shown in FIG. 4, the photometry unit 1 according to this embodiment includes a storage unit 11, the photo detection unit 8, amplifiers 12, a selection unit 13, an A/D converter 14, an absorbance calculation unit 15, a setting unit 16, an operation unit 17, and a display unit 18 to have a system control unit 10 as a core.

The storage unit 11 stores identifiers of the plurality of photo detectors (to be referred to as photo detector identifiers hereinafter) and those of a plurality of wavelength bands (to be referred to as wavelength band identifiers hereinafter) in association with each other. As each identifier, for example, its number or name is adopted. The storage unit 11 typically stores a database which associates photo detector identifiers and wavelength band identifiers with each other (to be referred to as an element/wavelength database hereinafter).

As described above, the photo detection unit 8 has the plurality of photo detectors 81, which are laid out two-dimensionally. Each photo detector 81 receives rays associated with its corresponding wavelength band, and generates an electrical signal according to the intensities of the received rays. To the plurality of photo detectors 81, a plurality of amplifiers 12 are respectively connected via the signal lines 84.

The plurality of amplifiers 12 are arranged on, for example, a single electronic broad. The amplifiers 12 amplify electrical signals from the photo detectors 81. To the plurality of amplifiers 12, the A/D converter 14 is connected via the selection unit 13.

The selection unit 13 selects photo detectors, which belong to wavelength bands used in absorbance calculations of measurement items of an object to be measured using the element/wavelength database. More specifically, the selection unit 13 selects, from the plurality of photo detectors 81, those corresponding to photo detector identifiers, which are associated with wavelength band identifiers of wavelength bands according to measurement items of a sample on the element/wavelength database. More particularly, the selection unit 13 is implemented by a switching unit 131 and collected data control unit 132. The switching unit 131 is arranged between the photo detection unit 8 and A/D converter 14. The switching unit 131 switches electrical connections between the plurality of photo detectors 81 in the photo detection unit 8 and the A/D converter 14, and can use electronic circuit elements such as multiplexers. The collected data control unit 132 controls the switching unit 131 to electrically connect the photo detectors 81 selected by the selection unit 13 to the A/D converter 14.

The A/D converter 14 A/D-converts analog electrical signals from the amplifiers 12 connected to the photo detectors 81 selected by the selection unit 13, thus generating digital electrical signals. To the A/D converter 14, the absorbance calculation unit 15 is connected.

The absorbance calculation unit 15 calculates absorbance related to measurement items of an object to be measured based on the digital electrical signals supplied from the A/D converter 14.

The setting unit 16 sets associations between the photo detector identifiers and wavelength band identifiers on the element/wavelength database according to an instruction from the user via the operation unit 17. Also, the setting unit 16 can change the associations between the photo detector identifiers and wavelength band identifiers in accordance with an instruction from the user via the operation unit 17.

The operation unit 17 accepts various commands and information inputs from the user. As the operation unit 17, a keyboard, mouse, switches, and the like can be used as needed.

The display unit 18 displays a screen to create the element/wavelength database and absorbance calculation results. As the display unit 18, for example, a CRT display, liquid crystal display, organic EL display, plasma display, or the like can be used as needed.

Figure 5:
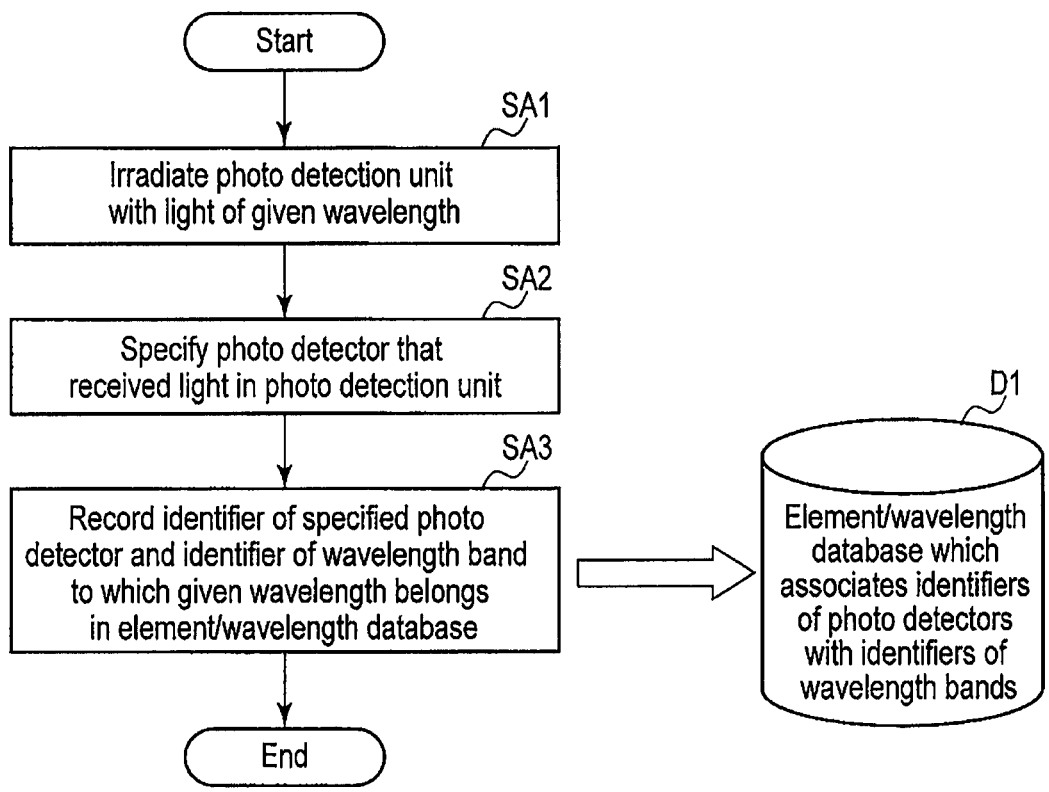
FIG. 5 is a flowchart showing the typical sequence of processing in an element/wavelength database generation stage of the automatic analyzer according to this embodiment.

An operation example of the automatic analyzer 100 in the element/wavelength database generation stage will be described below with reference to FIG. 5. FIG. 5 shows the typical sequence of processing in the element/wavelength database generation stage. The element/wavelength database is generated at the time of assembling of the photometry unit 1 or when wavelength accuracy deviations have occurred. Before the beginning of step SA1, the photo detection unit 8 is set at a position where it can receive rays from the spectroscope 7. For example, assuming that a wavelength band from 340 nm to 804 nm is indispensable to absorbance calculations, the photo detection unit 8 is set at a position where it can cover at least this wavelength band. Note that in order to prevent the wavelength band indispensable to absorbance calculations from failing to be covered due to occurrence of wavelength accuracy deviations, the photo detection unit 8 is preferably set to cover a wavelength band broader than the indispensable wavelength band.

As shown in FIG. 5, after the photo detection unit 8 is set, photometry is executed using light of a given wavelength. That is, the lamp 2 is controlled to emit light related to the given wavelength, and the photo detection unit 8 is irradiated with the light emitted by the lamp 2 via the spectroscope 7 (step SA1).

At this time, signal strengths of the respective photo detectors are measured to measure photo detection sensitivities of the respective photo detectors with respect to the given wavelength, thereby specifying the photo detectors 81, which received the light, from the plurality of photo detectors 81 (step SA2). The photo detectors 81 are specified by, for example, the following method. Initially, strengths of electrical signals from the plurality of photo detectors 81 are monitored. Then, photo detectors 81, which generated electrical signals having strengths larger than a prescribed threshold, are specified as those which received the rays. Also, photo detection sensitivities with respect to the given wavelength of the specified photo detectors are stored.

The setting unit 16 records the photo detectors 81 specified in step SA2 and the photo detection sensitivities with respect to the given wavelength in the element/wavelength database by associating their photo detector identifiers and a wavelength band identifier of a wavelength band, to which the given wavelength belongs, with each other (step SA3). Step SA3 will be described in detail below. In the element/wavelength database generation stage, the display unit 18 displays a screen to create an element/wavelength database (generation screen). On the generation screen, various GUI components required to associate the photo detector identifiers and wavelength band identifiers with each other are laid out. A wavelength band of light that can be received by each photo detector is decided according to, for example, the given wavelength and the wavelength width based on the size of the photo detection surface. The user makes an operation for associating the photo detector identifiers specified in step SA1 with the wavelength band identifier related to the given wavelength via the operation unit 17. The setting unit 16 associates the photo detector identifiers and the wavelength band identifier related to the given wavelength with each other according to this operation. Then, the setting unit 16 sets (records) the associated contents in an element/wavelength database D1.

Typically, a single wavelength band is associated with a plurality of photo detectors 81 which belong to a single channel. However, this embodiment is not limited to this. For example, a plurality of wavelength bands may be associated with a plurality of photo detectors 81 which belong to a single channel.

Figure 6:
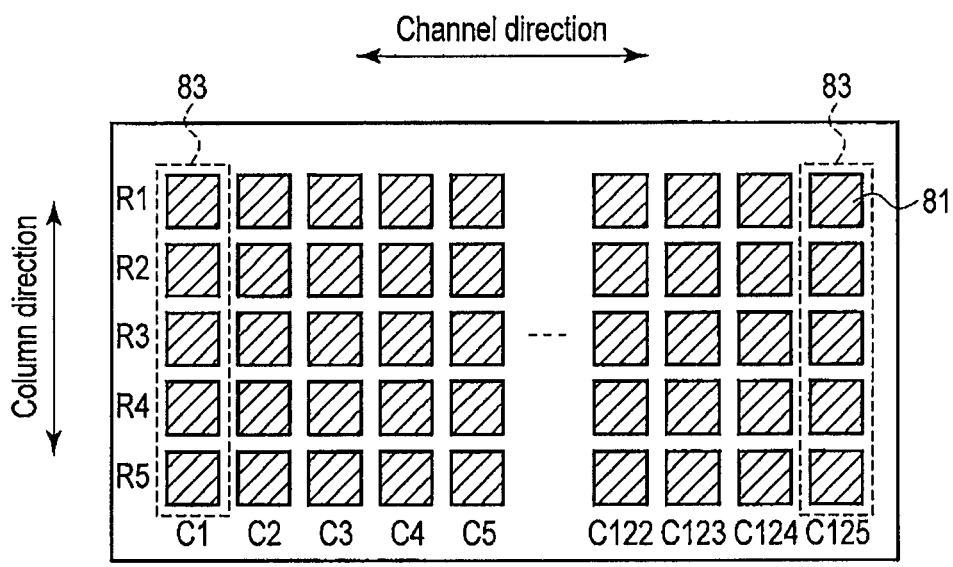
FIG. 6 is a view for explaining identifiers of the photo detectors and those of wavelength bands, which are associated with each other by a setting unit shown in FIG. 4.

FIG. 6 is a view for explaining the photo detector identifiers and wavelength band identifiers, which are associated with each other by the setting unit 16. As shown in FIG. 6, assume that 125 photo detectors 81 are laid out in the channel direction, and five photo detectors 81 are laid out in the column direction. For the purpose of associations, names are set for layout positions in the channel direction and those in the column direction. When a plurality of photo detector identifiers related to a plurality of photo detectors 81 which belong to a single channel are to be associated with a single wavelength band identifier, that is, when a wavelength band is associated with each photo detector column 83, the setting unit 16 associates the wavelength band identifier with names (photo detector identifiers) such as C1, C2, . . . , C125. In this case, the selection unit 13 selects the photo detector columns 83 using names such as C1, C2, . . . , C125. When wavelength band identifiers are associated with respective photo detectors 81, the setting unit 16 associates the wavelength band identifiers with names (photo detector identifiers) such as R1-C1, R1-C2, . . . , R5-C125. In this case, the selection unit 13 selects the photo detectors 81 using the names such as R1-C1, R1-C2, . . . , R5-C125.

Steps SA1 to SA3 are repetitively executed while changing a wavelength so as to associate wavelength band identifiers with all the photo detector identifiers.

For example, when a full measurement wavelength band ranges from 340 nm to 800 nm, and a wavelength width of each photo detector is ±2 nm, light of the given wavelength is repetitively measured to set a wavelength width to be ±2 nm with respect to each center wavelength while changing the center wavelength in 4-nm increments from 340 nm to 800 nm.

In this way, the element/wavelength database D1 is generated. Note that photo detector identifiers and wavelength band identifiers need not be associated with each other by irradiating all the photo detectors with light of the given wavelength in practice. For example, an unknown correspondence relationship between photo detector identifiers and wavelength band identifiers may be estimated from the given correspondence relationship between them.

Figure 7:
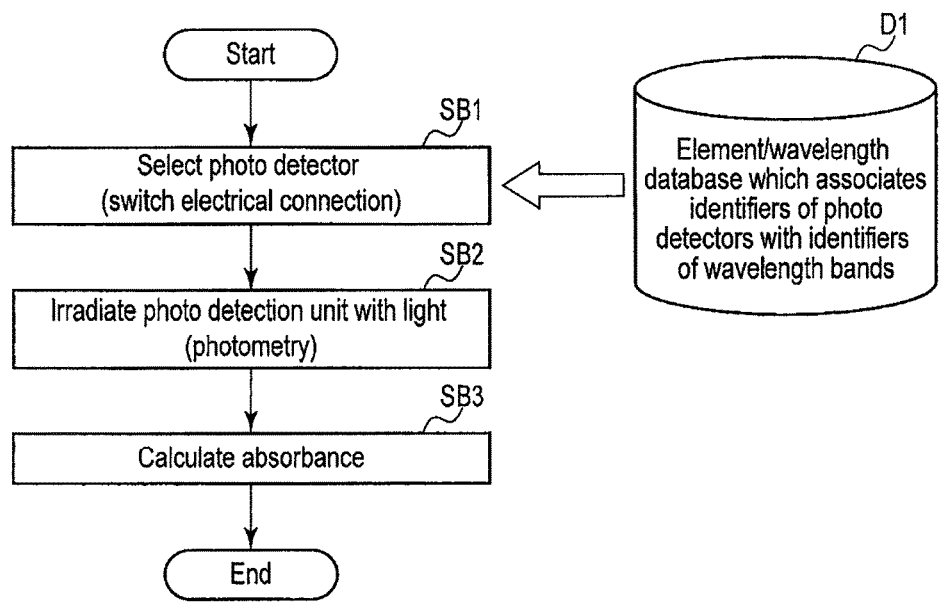
FIG. 7 is a flowchart showing the typical sequence of processing in a photometry stage of the automatic analyzer according to this embodiment.

An operation example of the automatic analyzer 100 at the time of photometry will be described below with reference to FIG. 7. FIG. 7 shows the typical sequence of processing of the automatic analyzer 100 in the photometry stage. Note that the photometry is executed each time the cuvette 22 passes the photometry position in the photometry unit 1. In each cuvette 22, measurement items are set by the system control unit 10 or the like according to an instruction from the user via the operation unit 17.

Note that absorbance calculations according to this embodiment are applicable to both a calculation method (1-wavelength calculations) using one wavelength band and that (2-wavelength calculations) using two discrete wavelength bands. However, for the sake of simplicity of the following description, assume that the absorbance calculations are 1-wavelength calculations, unless otherwise specified. A wavelength band used in absorbance calculations is typically broader than that for one channel. Therefore, even in case of the 1-wavelength calculations, a wavelength band used in absorbance calculations includes continuous wavelength bands for a plurality of channels. For example, when a wavelength band used in absorbance calculations ranges from 360 nm to 374 nm, continuous wavelength bands for three channels of 360 nm to 364 nm, 365 nm to 369 nm, and 370 nm to 374 nm are included.

In a stage before the cuvette 22 to be measured passes the photometry position PP, the selection unit 13 selects photo detectors 81 (step SB1). Step SB1 will be described in detail below. The collected data control unit 132 of the selection unit 13 specifies wavelength bands used in absorbance calculations. The wavelength bands used in absorbance calculations are decided according to measurement items. After the wavelength bands are specified, the collected data control unit 132 searches the element/wavelength database D1 using identifiers of the specified wavelength bands as search keys, thereby specifying photo detector identifiers, which are associated with the search keys on the element/wavelength database D1. Next, the collected data control unit 132 controls the switching unit 131 so that only electrical signals from photo detectors 81 corresponding to the specified identifiers are supplied to the A/D converter 14. The switching unit 131 electrically connects the specified photo detectors 81 to the A/D converter 14 under the control of the collected data control unit 132. Thus, the photo detectors 81 corresponding to measurement items are automatically selected. Note that the switching unit 131 can instantaneously switch electrical connections.

After the photo detectors 81 are selected, photometry is executed (step SB2). That is, the lamp 2 emits light. Light emitted by the lamp 2 transmits through a liquid mixture in the cuvette 22. The light transmitted through the liquid mixture is received by the photo detectors 81 via the spectroscope 7. The photo detectors 81, which received the light, generate electrical signals according to the received light. The generated electrical signals are supplied to the amplifiers 12. The amplifiers 12 amplify the supplied electrical signals. Only the photo detectors 81, which belong to wavelength bands used in absorbance calculations, are electrically connected to the A/D converter 14 via the amplifiers 12. That is, the electrical signals generated by the photo detectors 81, which belong to the wavelength bands used in absorbance calculations, are supplied to the A/D converter 14 via the amplifiers 12. The photo detectors 81, which belong to wavelength bands not used in absorbance calculations, are not connected to the A/D converter 14 via the amplifiers 12. Therefore, electrical signals generated by the photo detectors 81, which belong to the wavelength bands not used in absorbance calculations, are not supplied to the A/D converter 14, and are, for example, deleted. The A/D converter 14 converts the analog electrical signals from the photo detectors 81, which belong to the wavelength bands used in absorbance calculations, into digital electrical signals. The digital electrical signals are supplied to the absorbance calculation unit 15.

Figure 8:
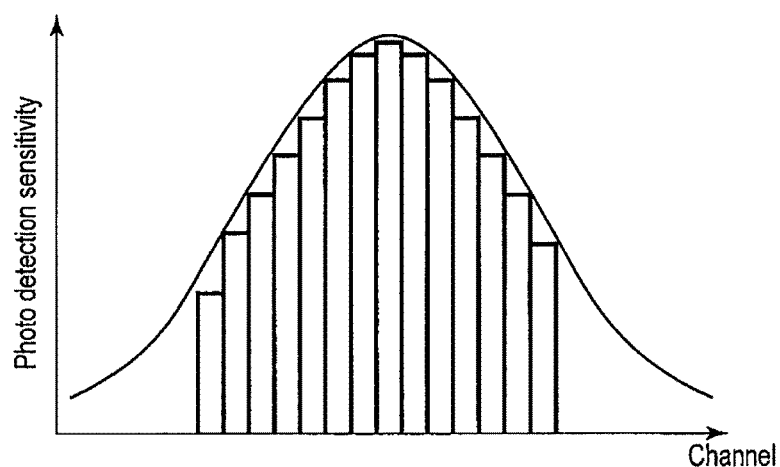
FIG. 8 is used in absorbance calculations in step SB3 in FIG. 7.

When the digital electrical signals are supplied, the absorbance calculation unit 15 calculates absorbance based on the electrical signals (step SB3). When a plurality of electrical signals from a plurality of channels are used in absorbance calculations, the absorbance calculation unit 15 may add the plurality of electrical signals by numeric calculations. Also, as shown in FIG. 8, photo detection sensitivities with respect to a desired wavelength (band) used in photometry are normally different depending on channels. Therefore, the absorbance calculation unit 15 may apply weighted additions according to photo detection sensitivities of a measurement wavelength to the electrical signals of the plurality of channels. For example, when electrical signals from N channels undergo weighted additions, an absorbance Abs is calculated according to:

$$\text{Abs} = \sum_n^N a_n \cdot x_n \quad (1)$$

where $X_n$ is a strength of an electrical signal of a channel n, and $a_n$ is a weighting coefficient (a photo detection sensitivity coefficient with respect to a predetermined wavelength) to the electrical signal of the channel n.

For example, a weighting coefficient assumes a larger value with increasing photo detection sensitivity with respect to the predetermined wavelength, and it assumes a smaller value with decreasing photo detection sensitivity. Alternatively, the weighting coefficient may be set according to absorption spectrum characteristics of an object to be measured (reaction solution), which are measured in advance. Alternatively, the weighting coefficient may be set by superposing both the photo detection sensitivity with respect to the predetermined wavelength and the absorption spectrum characteristics of the object to be measured (reaction solution). The calculated absorbance data are supplied to the system control unit 10. The system control unit 10 displays absorbance corresponding to the supplied data on the display unit 18.

As described above, the automatic analyzer 100 according to this embodiment stores the element/wavelength database which associates the photo detector identifiers with the wavelength band identifiers. Using this element/wavelength database, the automatic analyzer 100 selects, for respective measurement items, photo detectors 81 which receive light associated with wavelength bands according to the measurement items. The selected photo detectors 81 are electrically connected to the A/D converter 14. That is, only electrical signals from the selected photo detectors 81 are supplied to the A/D converter 14. The A/D converter 14 can convert only the electrical analog signals from the selected photo detectors 81 into the digital ones. Therefore, compared to the conventional case in which electrical analog signals from all photo detectors 81 are converted into the digital ones, the number of electrical signals to be A/D-converted can be reduced in this embodiment. That is, by limiting electrical signals to be supplied to the A/D converter 14, the processing volume of the A/D converter 14 can be reduced, thus reducing a load on the A/D converter 14.

Also, as described above, each of the photo detectors according to this embodiment has a small photo detection surface, and these elements are two-dimensionally and densely laid out. Therefore, each individual photo detector covers a narrower wavelength band than the conventional element. Hence, an optimal measurement wavelength band can be set for each measurement item. Therefore, according to this embodiment, the absorbance calculation precision can be improved.

Also, the automatic analyzer according to this embodiment can arbitrarily associate the photo detectors with wavelength bands, and can change correspondence between the photo detectors and wavelength bands. Therefore, according to this embodiment, even when wavelength accuracy deviations have occurred, the associations between the photo detectors and wavelength bands need only be changed without any position adjustments of the photo detectors. For this reason, the automatic analyzer according to this embodiment can correct wavelength accuracy deviations more easily than the conventional apparatus. Also, the automatic analyzer according to this embodiment can reduce cost required for position adjustments of photo detectors compared to the conventional apparatus.

As described above, the automatic analyzer according to this embodiment can reduce a load on the position adjustments of photo detectors.

(First Modification)

An automatic analyzer according to the first modification of this embodiment will be described below. Note that in the following description, the same reference numerals denote components and steps having substantially the same functions as those of this embodiment, and a redundant description will be given only when it is necessary.

As described above, wavelength bands used in absorbance calculations are decided according to types of measurement items. The storage unit 11 according to the modification stores an item/wavelength database which associates identifiers of a plurality of measurement items with those of a plurality of wavelength bands. The storage unit 11 according to the modification may combine the element/wavelength database and the item/wavelength database. That is, the storage unit 11 according to the modification may store a plurality of photo detector identifiers and a plurality of identifiers related to the plurality of measurement items (to be referred to as measurement item identifiers hereinafter) in association with each other. The photo detector identifiers and measurement item identifiers are associated with each other in an element/item database. The setting unit 16 according to the modification can associate measurement items identifiers with photo detector identifiers at the time of generation of the aforementioned element/wavelength database. Also, the setting unit 16 according to the modification can change associations between the photo detector identifiers and measurement item identifiers in accordance with an instruction from the user via the operation unit 17.

An operation example of the automatic analyzer according to the first modification at the time of photometry will be described below with reference to FIG. 9. FIG. 9 shows the typical sequence of processing in a photometry stage of the automatic analyzer according to the first modification. Note that differences between FIGS. 5 and 9 lie in steps SC1 and SC2. Therefore, only steps SC1 and SC2 will be described below.

As shown in FIG. 9, the collected data control unit 132 of the selection unit 13 recognizes measurement items set in the cuvette 22 to be measured before this cuvette 22 passes the photometry position PP (step SC1). The measurement items can be recognized by referring to a measurement order managed by, for example, the system control unit 10.

After the measurement items are recognized, the collected data control unit 132 selects photo detectors 81 according to the recognized measurement items (step SC2). Step SC2 will be described in detail below. The selection method of the photo detectors according to measurement items includes a method using an element/item database D2 and that using the element/wavelength database D1 and an item/wavelength database D3.

When the element/item database D2 is used, the collected data control unit 132 searches the element/item database D2 using the measurement item identifiers of the recognized measurement items as search keys, thereby specifying photo detector identifiers associated with the search keys on the element/item database D2. After the photo detector identifiers are specified, the collected data control unit 132 controls the switching unit 131 to electrically connect the photo detectors 81 corresponding to the specified photo detector identifiers to the A/D converter 14. Thus, the photo detectors 81 according to the measurement items can be selected.

When the element/wavelength database D1 and item/wavelength database D3 are used, the collected data control unit 132 searches the item/wavelength database D3 using the measurement item identifiers of the recognized measurement items as search keys, thus specifying wavelength band identifiers associated with the search keys on the item/wavelength database D3. Next, the collected data control unit 132 searches the element/wavelength database D1 using the specified wavelength band identifiers as search keys, thus specifying photo detector identifiers associated with the search keys on the element/wavelength database D1. After the photo detector identifiers are specified, the collected data control unit 132 controls the switching unit 131 to electrically connect the photo detectors 81 corresponding to the specified photo detector identifiers to the A/D converter 14. Thus, the photo detectors 81 according to the measurement items can be automatically selected.

As described above, the automatic analyzer according to the first modification associates measurement items with photo detectors directly or indirectly via wavelength bands. Therefore, the automatic analyzer according to the first modification can select photo detectors more quickly than that according to this embodiment.

(Second Modification)

In the above embodiment, by selecting the photo detectors 81, electrical signals to be used in absorbance calculations are selected. However, this embodiment is not limited to this. An automatic analyzer according to the second modification selects electrical signals in an absorbance calculation stage. The automatic analyzer according to the second modification will be described below. Note that in the following description, the same reference numerals denote components having substantially the same functions as those of this embodiment, and a redundant description will be given only when it is necessary.

Figure 10:
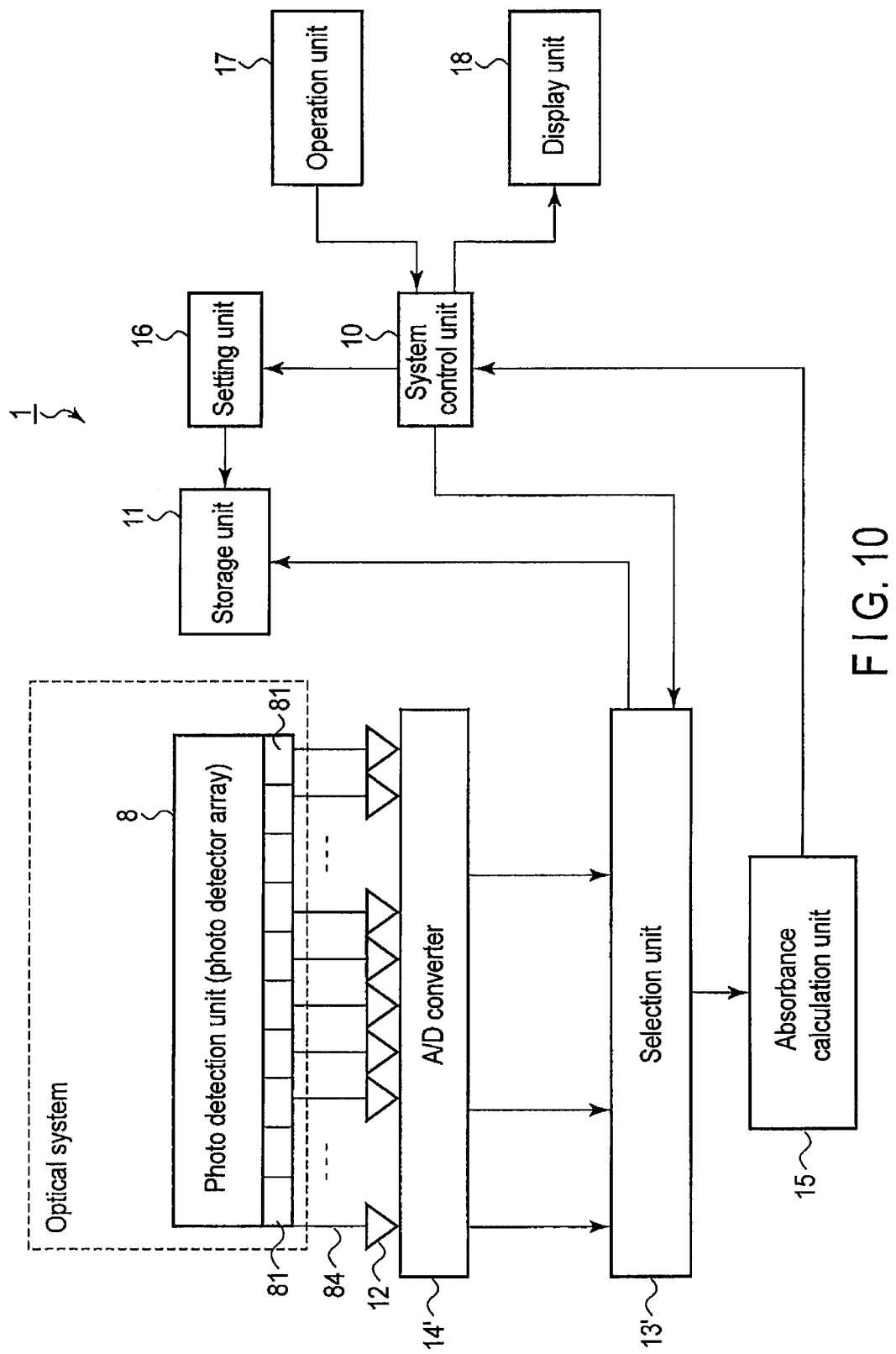
FIG. 10 is a block diagram showing the overall arrangement of a photometry unit according to the second modification of this embodiment.

FIG. 10 shows the overall arrangement of the photometry unit 1 according to the second modification. As shown in FIG. 10, all photo detectors 81 included in the photo detection unit 8 are electrically connected to an A/D converter 14' via the amplifiers 12. The A/D converter 14' converts analog electrical signals from all the photo detectors 81 into digital signals. The A/D converter 14' is electrically connected to a selection unit 13'. The selection unit 13' selects electrical signals related to wavelength bands used in absorbance calculations from those of all the photo detectors. For example, the selection unit 13' selects electrical signals on software using the element/wavelength database. To the selection unit 13', the absorbance calculation unit 15 is connected. The absorbance calculation unit 15 calculates absorbance based on the electrical signals selected by the selection unit 13'.

As described above, the automatic analyzer according to the second modification can select electrical signals from photo detectors, which belong to wavelength bands required for absorbance calculations, without changing the mechanical arrangement up to the A/D converter.

Some embodiments of the present invention have been explained. These embodiments are presented for the exemplary purpose only, and do not intend to limit the scope of the invention. These novel embodiments can be practiced in various other aspects, and can undergo various omissions, replacements, and changes without departing from the spirit of the invention. These embodiments and modifications are included in the scope and spirit of the invention, and are also included in the inventions described in the scope of the claims and their equivalent scopes.

For example, in FIG. 2, the optical layout of the infrared cut filter 3, lens 4, slit 5, slit 6, and the like can be changed, and the infrared cut filter 3 and slit 5 may be omitted. Also, a one-dimensional layout of the photo detectors 81 can be used. In this case, the photo detectors are laid out only in the channel direction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An automatic analyzer comprising: a light source configured to emit light;
    a spectroscope configured to disperse light, which is emitted by the light source and is transmitted through a liquid mixture of a sample and a reagent, into different wavelengths;
    a photo detector including a plurality of photo detectors which receive light from the spectroscope, each of the photo detectors configured to receive light related to a wavelength band corresponding to a location of that photo detector, and to generate a signal according to the received light, the plurality of photo detectors being two-dimensionally laid out along a channel direction parallel to a diffusion direction of wavelengths of light from the spectroscope and a column direction orthogonal to the channel direction;

a memory configured to store a plurality of photo detector identifiers related to the plurality of photo detectors and a plurality of wavelength band identifiers in association with each other and to associate wavelength band identifiers related to a same wavelength band with photo detectors belonging to a same channel among the plurality of photo detectors;

a selector configured to select a specific plurality of specific photo detectors from the photo detectors, the specific plurality of photo detectors corresponding according to a specific photo detector identifier associated with a wavelength band identifier of a measurement wavelength band corresponding according to a measurement item of the sample;

a calculation processor configured to calculate an absorbance related to the measurement item based on a signal from a selected specific photo detector, wherein the calculation processor generates a weighted-sum signal obtained by weighting and adding, across a specific plurality of channels corresponding to the specific plurality of photodetectors, signal strengths of the specific plurality of photo detectors based on photo detection sensitivities corresponding to channel positions of the specific plurality of channels with respect to the measurement wavelength band of the plurality of specific photo detectors, and calculates the absorbance based on the generated weighted-sum signal, wherein when a plurality of electrical signals from the specific plurality of photo detectors for the specific plurality of channels N are used in absorbance calculations for the sample, the calculation processor generates the weighted-sum signal by weighting and adding the signal strengths of the photo detectors included in the specific photo detector based on the photo detection sensitivities corresponding to channel positions with respect to the measurement wavelength band of the photo detectors and absorption spectrum information of a measurement item, and calculates the absorbance based on the generated weighted-sum signal Abs according to the following equation:

$$\text{Abs} = \sum_{n}^{N} a_n \cdot X_n$$

where $X_n$ is a strength of an electrical signal of a channel n, and $a_n$ is a weighting coefficient which corresponds to a photo detection sensitivity coefficient with respect to a predetermined wavelength band to the electrical signal of the channel n, and wherein weighting coefficients are set to a larger value with increasing photo detection sensitivity with respect to the predetermined wavelength band and a smaller value with decreasing photo detection sensitivity with respect to the predetermined wavelength band.

2. The automatic analyzer according to claim 1, wherein the selector includes:
  a switch configured to switch connections between the photo detectors and the calculation processor; and
  a controller configured to control the switch to connect the specific plurality of photo detector detectors to the calculation processor.

3. The automatic analyzer according to claim 2, wherein the switch is arranged between a plurality of amplifiers and an A/D converter,
  the plurality of amplifiers are respectively connected to the plurality of photo detectors, and amplify the signals from the plurality of photo detectors, and
  the A/D converter converts only analog signals from specific amplifiers among the amplifiers into digital signals, the specific amplifiers being connected to the specific plurality of photo detectors.

4. The automatic analyzer according to claim 1,
  wherein the memory further stores the plurality of photo detector identifiers and a plurality of measurement item identifiers related to a plurality of measurement items in association with each other, and
  the selector selects the specific plurality of photo detectors corresponding to the specific wavelength band identifier associated with a measurement item identifier related to the measurement item of the sample.

5. The automatic analyzer according to claim 4,
  wherein the memory further stores the plurality of wavelength band identifiers and the plurality of measurement item identifiers related to the plurality of measurement items in association with each other, and
  the selector specifies the wavelength band identifier associated with the measurement item identifier related to the measurement item of the sample on the memory, and selects the specific plurality of photo detectors corresponding to the specific photo detector identifiers associated with the specified wavelength band identifier on the memory.

6. The automatic analyzer according to claim 1, wherein the photo detectors are arrayed at equal intervals, and
  a width between two neighboring photo detectors among the photo detectors is set to be not more than about 20% of a width of each photo detector.

7. The automatic analyzer according to claim 1, wherein the weighting coefficients are set according to absorption spectrum characteristics of a sample to be measured, which are measured in advance.

8. The automatic analyzer according to claim 1, wherein the weighting coefficients are set by superposing both the photo detection sensitivity with respect to the predetermined wavelength band and absorption spectrum characteristics of a sample to be measured.

* * * * *